United States Patent
Girardon et al.

(10) Patent No.: US 6,178,921 B1
(45) Date of Patent: Jan. 30, 2001

(54) METHOD OF IMPROVING BREEDING CONDITIONS IN NEWBORN PIGS

(75) Inventors: Philippe Girardon, Versailles; Patrick Herpin, L'Hermitage, both of (FR)

(73) Assignee: L'Air Liquide, Paris Cedex (FR)

( * ) Notice: Under 35 U.S.C. 154(b), the term of this patent shall be extended for 0 days.

(21) Appl. No.: 09/289,985

(22) Filed: Apr. 13, 1999

(30) Foreign Application Priority Data

Apr. 16, 1998 (FR) .................................................. 98 04755

(51) Int. Cl.$^7$ ...................................................... A01K 1/03
(52) U.S. Cl. ................................................................ 119/420
(58) Field of Search ........................... 119/420, 482, 119/417, 448, 503, 508, 311, 317, 315; 600/22; 128/204.23

(56) References Cited

U.S. PATENT DOCUMENTS

| | | | |
|---|---|---|---|
| 3,553,426 | * | 1/1971 | Fink ...................................... 219/406 |
| 3,618,734 | * | 11/1971 | Khan .................................... 119/318 |
| 3,779,210 | * | 12/1973 | Blair ..................................... 119/457 |
| 3,821,947 | * | 7/1974 | Schossow .............................. 600/22 |
| 3,878,570 | * | 4/1975 | Donnelly .............................. 600/22 |
| 4,292,929 | * | 10/1981 | Tellers .................................. 119/518 |
| 4,328,793 | * | 5/1982 | Martin .................................. 600/22 |
| 4,332,214 | * | 6/1982 | Cunningham ....................... 119/472 |
| 4,343,304 | * | 8/1982 | Hickmann ............................ 119/420 |
| 4,458,674 | * | 7/1984 | Lemburg et al. ..................... 600/22 |
| 4,495,892 | | 1/1985 | Jodar et al. .......................... 119/482 |
| 4,509,505 | * | 4/1985 | Mercey et al. ....................... 600/22 |
| 4,539,984 | * | 9/1985 | Kiszel et al. ..................... 128/204.23 |
| 4,796,605 | * | 1/1989 | Sasaki et al. ......................... 600/22 |
| 4,941,431 | | 7/1990 | Anderson et al. ................... 119/420 |
| 5,012,763 | * | 5/1991 | Morrison ............................. 119/302 |
| 5,074,248 | * | 12/1991 | Loader ................................. 119/505 |
| 5,140,947 | * | 8/1992 | Bruce .................................. 119/502 |
| 5,162,038 | * | 11/1992 | Wilker ................................. 600/22 |
| 5,316,542 | * | 5/1994 | Koch et al. .......................... 600/22 |
| 5,330,415 | * | 7/1994 | Storti et al. ......................... 600/22 |
| 5,336,156 | * | 8/1994 | Miller et al. ........................ 600/22 |
| 5,470,212 | * | 11/1995 | Pearce ................................. 119/311 |
| 5,582,574 | * | 12/1996 | Cramer ................................ 600/21 |
| 5,773,287 | * | 6/1998 | Binder ............................. 435/303.1 |
| 5,823,143 | * | 10/1998 | Wilson ................................ 119/312 |
| 5,843,404 | * | 12/1998 | Koch et al. .......................... 424/934 |
| B1 4,361,137 | * | 2/1997 | Grosholz .............................. 600/22 |

FOREIGN PATENT DOCUMENTS 2710816    4/1995   (FR) .

OTHER PUBLICATIONS

White, et al. "Increasing piglet survival through an improved farrowing management protocol" 1996, pp. 491–495.
Condensed Chemical Dictionary, ninth edition, pp. 20–21.*

* cited by examiner

Primary Examiner—Michael J. Carone
Assistant Examiner—Judith A. Nelson
(74) Attorney, Agent, or Firm—Nixon Peabody LLP

(57) ABSTRACT

Method of improving the breeding conditions for pigs, according to which the piglets are placed after birth in a closed or semiclosed chamber, a gaseous mixture containing oxygen is injected into the chamber, characterized in that the oxygen content of the gaseous mixture is between 25 and 50%.

8 Claims, 3 Drawing Sheets

METHOD OF IMPROVING BREEDING CONDITIONS IN NEWBORN PIGS

BACKGROUND OF THE INVENTION

1. Field of the Invention

The present invention relates to methods which make it possible to improve the breeding conditions for piglets (newborn pigs).

2. Description of Related Art

It is known that the productivity of pig farms in France and worldwide remains limited by a high postnatal mortality, this being in spite of the improvements which have been made in the past few years relating to breeding techniques, especially in terms of nutrition and control of the surroundings and of the pathologies affecting the species.

Thus, by way of illustration, the numbers for the amount of losses for 1996 in France are up to about 18% of the total number of newborns, which corresponds to about 5% of stillborn piglets, while 13% of the liveborn piglets die between birth and weaning, of which half during the first 48 hours following birth.

While a number of causes have been put forward to explain this relatively high mortality rate, causes such as the crushing of the newborns by the sow, sensitivity to cold and also certain pathologies, the fact remains that a quarter of this postnatal mortality can, it seems, be attributed to a phenomenon of hypoxia resulting from farrowing and affecting the thermoregulatory function and the vitality of the newborn (see for example the article by P. Herpin et al. which appeared in Journées sur la Recherche Porcine en France in 1997, page 29).

Indeed, during farrowing in sows, which can last for several hours, the repeated uterine contractions can reduce exchanges between the fetus and the placenta, which can cause a drop in blood flow rate across the placenta and sometimes even a premature detachment of the placenta or a rupture of the umbilical cord. It is known that this risk increases with the duration of farrowing, with the size of the litter, but also with the order of birth within this litter.

It is known, moreover, that the lightest piglets are more subject to this hypoxia phenomenon. It should also be noted that even if the piglets are alive after farrowing, they can suffer and retain sequelae from this neonatal hypoxia because a few minutes of anoxia is sufficient to inhibit the respiratory centers and to cause irreversible legions in the brain of the piglets.

The degree of hypoxia in the piglets at birth may be measured in particular by one or more of the following blood factors:

the partial pressure of oxygen or of $CO_2$;

the pH;

the lactate content.

A hypoxia is then characterized by a low pH, a high lactatemia and a high partial pressure of $CO_2$.

It can also be stated that one of the consequences of the phenomenon of hypoxia in piglets, through the fact that it reduces the physical vitality of the animal (stability, attempts to stand up), is to delay the piglets' first contact with the teat and therefore the first sucking which is necessary not only in terms of supply of energy for thermoregulation, but also for acquiring immunoglobulins.

Document FR-A-2,710,816 provides a method and a plant for improving the breeding conditions for animals in a closed or semiclosed chamber, such as using an injection of oxygen at periodic intervals or during selected periods such as the meals, service periods or alternatively periods preceding or following birth, the content of oxygen in the surrounding air then being maintained between 20.5 and 21.5%. The objective sought by this document is to solve a problem of mortality of the individuals, especially in a period of heat, and for example for newborns during premature births or births after term.

The approach followed by this document is to maintain the oxygen level around the atmospheric content and is therefore to adjust this content to around 21%, the oxygen in the surrounding atmosphere indeed having a tendency to decrease substantially in intensive breedings because of respiration by the animals.

The approach of this document is therefore rather attached to a renewal of the surrounding atmosphere which becomes depleted over time.

There may also be mentioned the case of the document FR-A-2,645,403 which provides a method of breeding living beings in an oxygenated medium in order to increase their size, the objective being to make it possible to increase the size of the animals "up to several ten of times" depending on the species and "to cause them to gain more meat".

Besides the fact that the document is based on reasoning which is not very scientific (such as mentioning the size of dragonflies and other crickets in the Jurassic period), it remains silent on the oxygen conditions to be applied in order to achieve such objectives, and a fortiori completely ignores the problems of postnatal mortality.

SUMMARY AND OBJECTS OF THE INVENTION

The present invention aims to solve the problems mentioned above.

To do this, the method for improving breeding conditions for pigs according to the invention, according to which:

the piglets are placed after birth in a closed or semiclosed chamber;

a gaseous mixture containing oxygen is injected into the chamber;

is characterized in that the oxygen content of the gaseous mixture is between 25 and 50%.

The piglet is therefore according to the invention subjected, in the chamber, to a highly overoxygenated atmosphere since it contains between 25 and 50% oxygen.

The work successfully carried out by the applicant has therefore made it possible to demonstrate that it is advantageous, in order to improve the productivity level of pig breeding, not to carry out a simple renewal of the breeding air as commonly reported in the literature, but to carry out a significant overoxygenation of the newborns since it is up to levels of several tens of % of oxygen.

It should be noted that, surprisingly, in spite of such very high levels, no toxicity of the oxygen is observed (lungs, airways and the like).

The method according to the invention can, moreover, adopt one or more of the following characteristics:

the oxygen content of the gaseous mixture is in the range from 30 to 50%, and still more preferably in the range from 35 to 45%;

the piglets are placed in the chamber within the hour following birth;

the piglets are placed in the chamber within 30 min following birth, and still more preferably within 20 min following birth, or even immediately after birth;

the piglets are kept in the chamber, in the atmosphere consisting of the gaseous mixture, for a period of 5 to 30 min;

the piglets are kept in the chamber, in the atmosphere consisting of the gaseous mixture, for a period of 10 to 25 min;

the gaseous mixture, previously injected into the chamber, was made humid;

said gaseous mixture containing 25 to 50% oxygen is used during the whole or part of the farrowing proper.

Other characteristics and advantages of the invention will emerge from the following description given by way of illustration with no limitation being implied, with reference to the accompanying drawings.

DETAILED DESCRIPTION OF PREFERRED EMBODIMENTS

In all the cases of piglets treated according to the invention, the animals were introduced 4 minutes after birth into a chamber containing nitrogen and an oxygen content of 40%, and remained in this chamber for about 20 minutes.

The treatment is applied "intra-litter", that is to say within the same litter, the same number of piglets is put in each batch and that after the treatment, the piglets treated according to the invention are replaced with their mother and raised under the same conditions as the control piglets.

Figure 1:
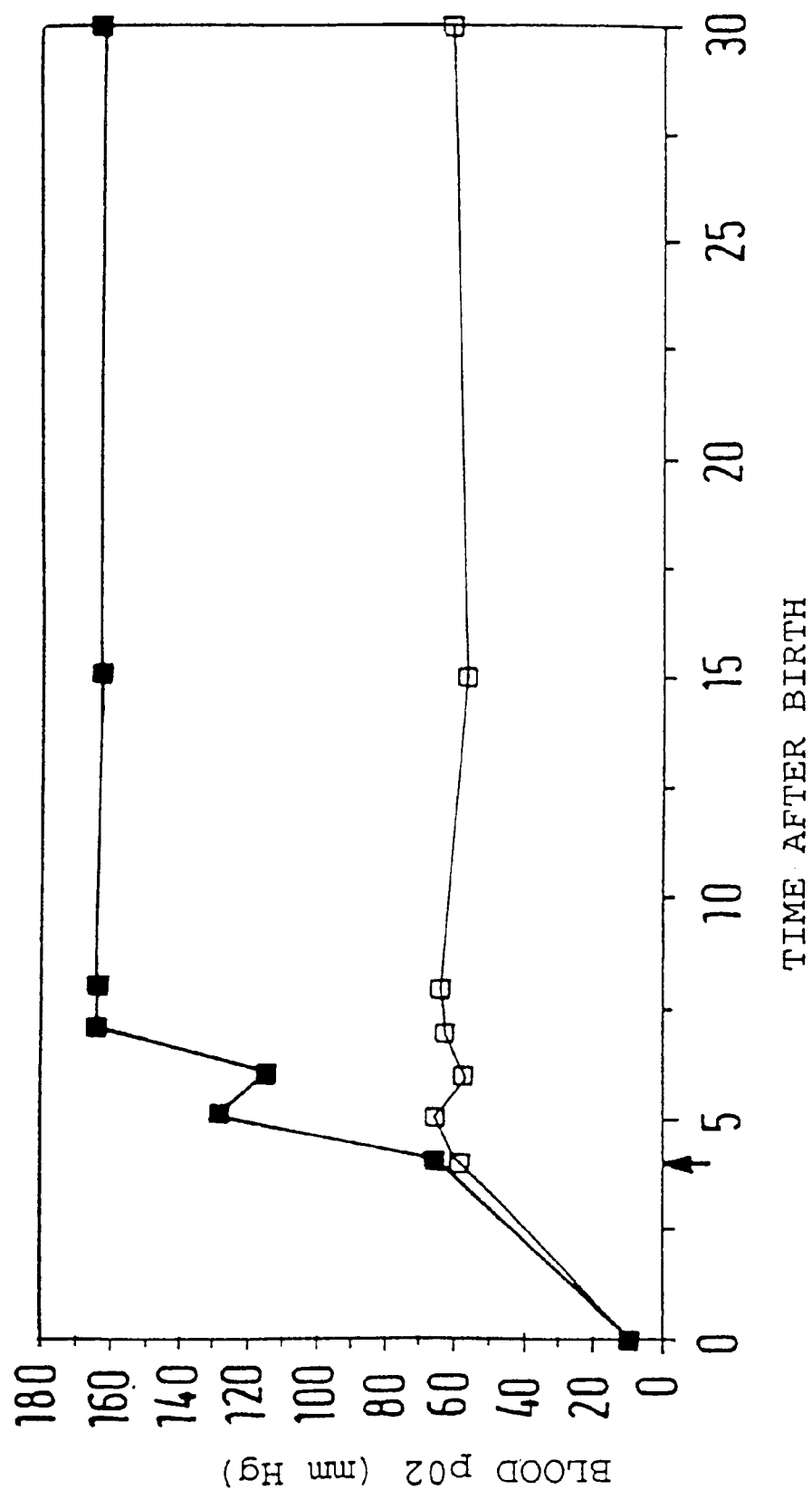
FIG. 1 represents the comparative variation of the blood oxygen partial pressure as a function of time after birth (in minutes) for two batches of piglets, one batch oxygenated after birth according to the invention and a second control batch not treated according to the invention.
Figure 2:
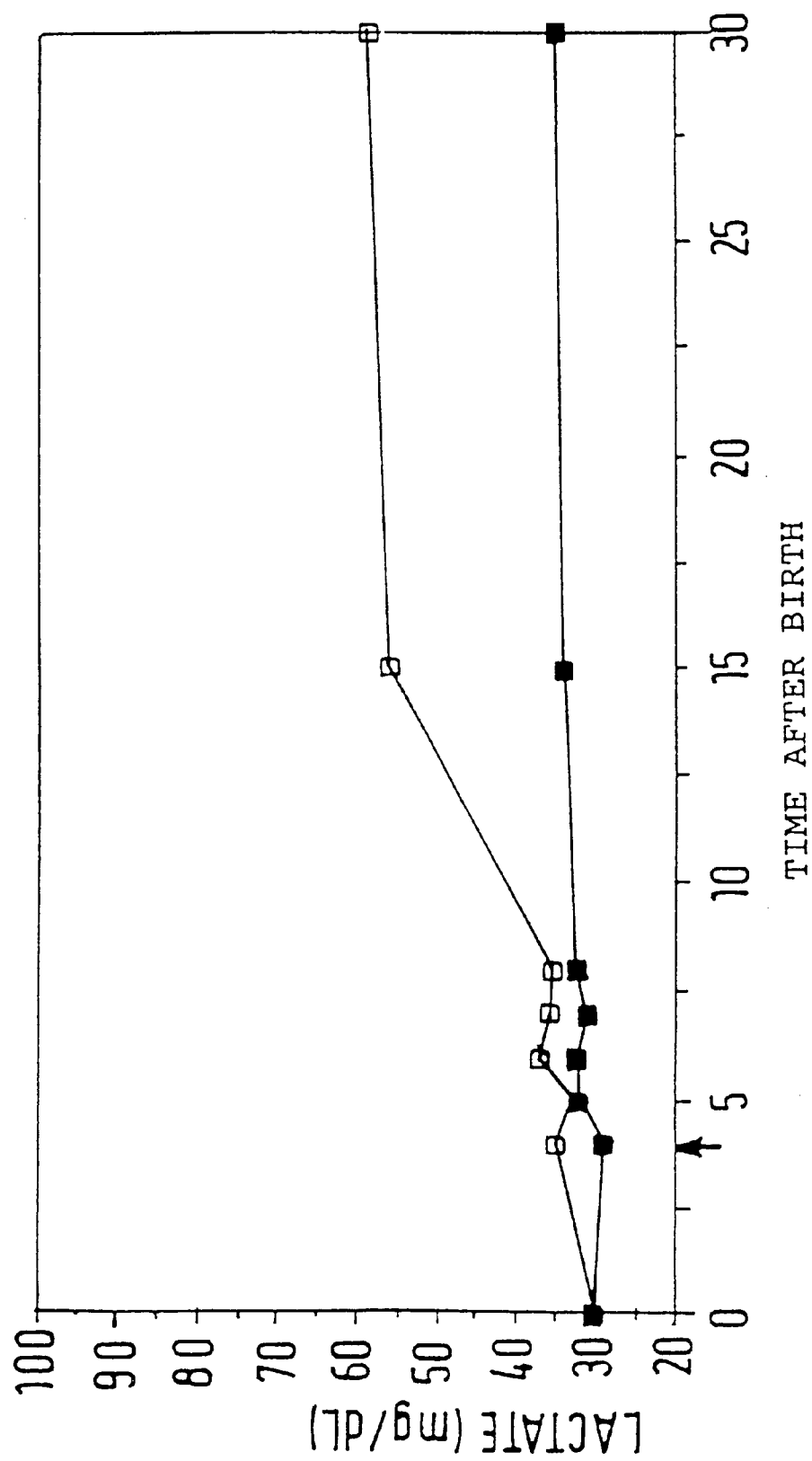
FIG. 2 represents the comparative variation of the blood lactate level as a function of time after birth (in minutes) for two batches of piglets, one batch oxygenated after birth according to the invention and a second control batch not treated according to the invention.

An arrow can therefore be seen, in FIGS. 1 and 2, on the x-axis showing 4 minutes and representing the time following birth when the piglets are placed in the chamber to be brought into contact with the treatment atmosphere.

For these two figures, the curve with solid squares was obtained for the batch of piglets oxygenated according to the invention, while the curve with empty squares was obtained for the control batch of piglets.

The results illustrated for these two figures, in terms of blood oxygen partial pressure and in terms of blood lactate level, clearly demonstrate an improvement in the oxygenation of the tissues (partial pressure of oxygen increased by the treatment, postnatal increase in the lactate level controlled), and therefore a substantial influence on the energy metabolism in the animals.

Figure 3:
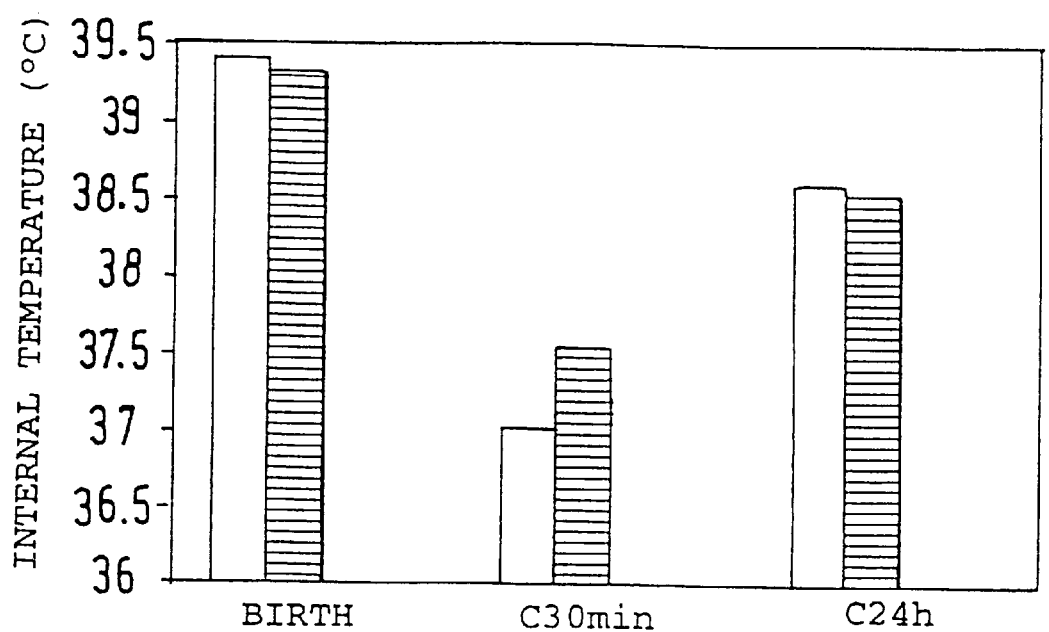
FIG. 3 illustrates the results obtained in terms of internal temperature of the piglets (at birth, after 30 min and after 24 h) for two batches of piglets, a first batch oxygenated after birth according to the invention and a second control batch not treated according to the invention.

As regards the results of internal temperature represented in FIG. 3, for which the results of the control batch are represented in empty bars while the results of the batch according to the invention are represented in solid bars.

In a completely coherent manner, these internal temperature results show that the internal temperature in the piglets drops naturally during the first 30 minutes following birth, before rising gradually because of the thermoregulatory function (see variation of the empty bars).

It can be observed that the oxygenation treatment according to the invention significantly limits the temperature measured after 30 min, the treatment according to the invention suppressing, as already seen, the negative effects of asphyxia but also improving in this case the thermoregulatory capacities immediately after birth.

It is possible to think that the oxygen therapy treatment applied stimulates the thermoregulatory function promoting the oxidative metabolism, that is to say the oxidation of glucose by reducing the production of lactate, which allows a higher production of energy at the time of maximum energy expenditure by the piglets.

After 24 h, the temperature results for the two batches are comparable, but it is understood that these results relate only to the animals which survived.

Figure 4:
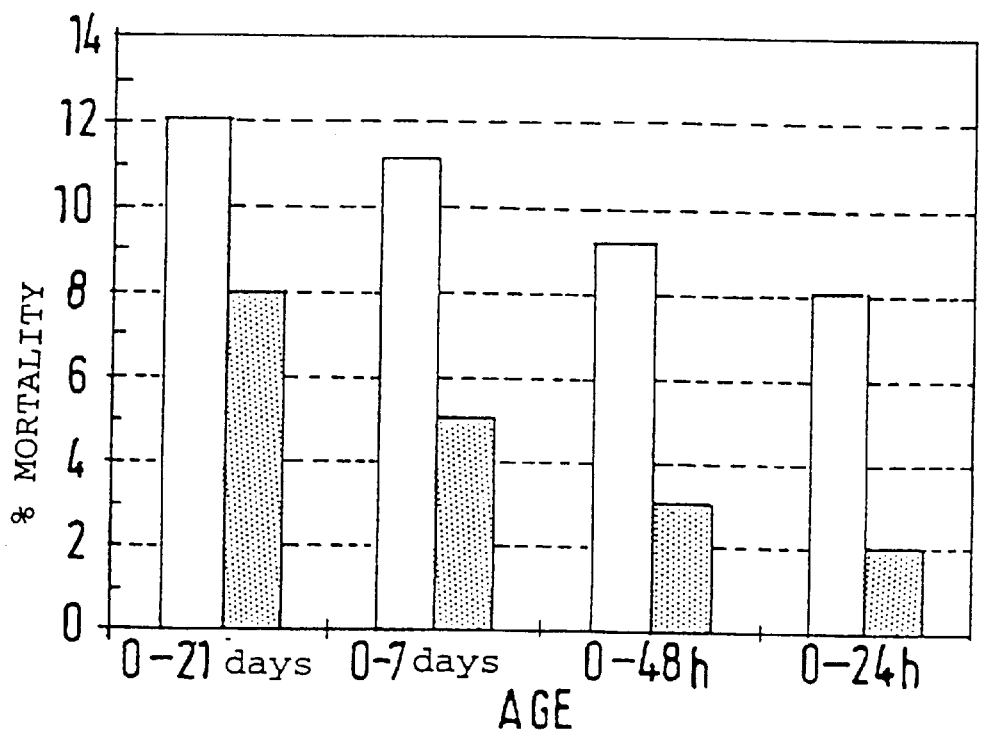
FIG. 4 illustrates the comparative results of mortality rates after 24 h, 48 h, 7 days and 21 days, here again for two batches of piglets, a first batch oxygenated after birth according to the invention and a second control batch not treated according to the invention.

However, as illustrated in FIG. 4 (same representation of the two batches as for FIG. 3), the rate of survival of the piglets after 24 h, 48 h, 7 days and 21 days (that is to say at the time of weaning) thereby becomes quite considerably enhanced: the mortality rate being reduced by a third after 21 days.

It will in fact be noted that the oxygenation treatment according to the invention has no effect on the weight of the individuals which survived after weaning; there are therefore obtained for the batches tested the same weight at 21 days and the same growth up to the slaughtering stage for the control batch and for the batch oxygenated according to the invention.

Although the present invention has been described in relation to specific embodiments, it is not thereby limited but is on the contrary subject to modifications and variations which will appear to persons skilled in the art in the context of the claims below.

What is claimed is:

1. Method of increasing the survival rate of piglets comprising the steps of:

placing piglets after birth in a closed or semiclosed chamber;

injecting a gaseous mixture comprising a content of oxygen into the chamber;

wherein the oxygen content of the gaseous mixture is between 30 and 50%.

2. Method according to claim 1 wherein, the oxygen content of the gaseous mixture is in the range from about 35 to 45%.

3. Method according to claim 1, further comprising placing the piglets in the chamber at a time within about an hour following birth.

4. Method according to claim 3, wherein the time when the piglets are placed in the chamber is within about 30 min following birth.

5. Method according to claim 3, wherein the time when the piglets are placed in the chamber is within about 20 min following birth.

6. Method according to claim 1, further comprising keeping the piglets in the chamber in an atmosphere for a period of about 5 to 30 min.

7. Method according to claim 6, wherein the piglets are kept in the chamber in an atmosphere for a period of about 10 to 25 min.

8. Method according to claim 1, further comprising making the gaseous mixture injected into the chamber humid beforehand.

* * * * *